United States Patent [19]

Herring

[11] Patent Number: 4,725,673

[45] Date of Patent: Feb. 16, 1988

[54] PLASMA FRACTION PURIFICATION USING SILICA RESIN BOUND TO A LIGAND

[75] Inventor: Steven W. Herring, San Dimas, Calif.

[73] Assignee: Alpha Therapeutic Corporation, Los Angeles, Calif.

[21] Appl. No.: 902,155

[22] Filed: Aug. 29, 1986

[51] Int. Cl.⁴ .................... A61K 35/16; A61K 37/02; C07K 3/20

[52] U.S. Cl. .................................. 530/381; 530/384; 530/417; 530/830; 536/21; 536/51

[58] Field of Search ............... 530/830, 387, 384, 417; 424/101; 536/21

[56] References Cited

U.S. PATENT DOCUMENTS

| 4,081,431 | 3/1978 | Stephan | 530/384 |
| 4,136,094 | 1/1979 | Condie | 530/387 X |
| 4,170,590 | 10/1979 | Stephan | 530/384 X |
| 4,272,523 | 6/1981 | Kotitschke | 530/384 X |
| 4,305,870 | 12/1981 | Liu | 530/381 X |
| 4,322,403 | 3/1982 | Bunnig | 530/387 X |
| 4,364,861 | 12/1982 | Mitra | 530/384 |
| 4,411,794 | 10/1983 | Schwinn | 530/384 |
| 4,472,303 | 9/1984 | Tanihara | 530/387 X |
| 4,503,039 | 3/1985 | Kotitschke | 424/101 |
| 4,639,513 | 1/1987 | Hou | 530/387 |

OTHER PUBLICATIONS

D. S. Pepper and C. Prowse, "Chromatography of Human Prothrombin Complex on Dextran Sulfate Agarose," *Thrombosis Research*, vol. 11, No. 5, 1977, pp. 687–692.

L.-O. Andersson, et al., "Purification and Characterization of Human Factor IX," *Thrombosis Research*, vol. 7, 1975, pp. 451–459.

D. Menache, et al., "Coagulation Factor IX Concentrate: Method of Preparation and Assessment of Potential in vivo Thrombogenicity in Animal Models," *Blood*, vol. 64, No. 6, Dec. 1984, pp. 1220–1227.

S. P. Bajaj, et al., "A Simplified Procedure for Purification of Human Prothrombin Factor IX and Factor X," *Preparative Biochemistry*, 11 (4), 1981, pp. 397–412.

A Catalog of SERVA Fine Biochemical Inc. of Westbury, New York (pp. LC2, LC3 and LC4).

Paper entitled "Covalent Attachment of Heparin to Silica: Affinity Purification of Antithrombin III from Human Plasma by Heparin–Silica–Column", for the Tenth International Symposium on Column Liquid Chromatography, San Francisco, California, May 18–23, 1986, p. 23.

J. P. Miletich, et al., "The Synthesis of Sulfated Dextran Beads for the Isolation of Human Plasma Coagulation Factors II, IX and X," *Analytical Biochemistry*, vol. 105, 1980, pp. 304–310.

*Primary Examiner*—Howard E. Schain
*Attorney, Agent, or Firm*—Christie, Parker & Hale

[57] ABSTRACT

There is provided, in accordance with practice of this invention, a process for separating Factor IX and/or Factor X from an impure protein fraction containing protein in addition to Factors IX and X. A silica resin coupled with a ligand capable of binding Factor IX and/or Factor X is provided. An aqueous solution of the impure protein fraction is applied to the ligand-coupled silica resin to thereby bind the Factor IX and/or Factor X to the resin. The Factor IX and/or Factor X is then recovered from the resin by elution.

28 Claims, 1 Drawing Figure

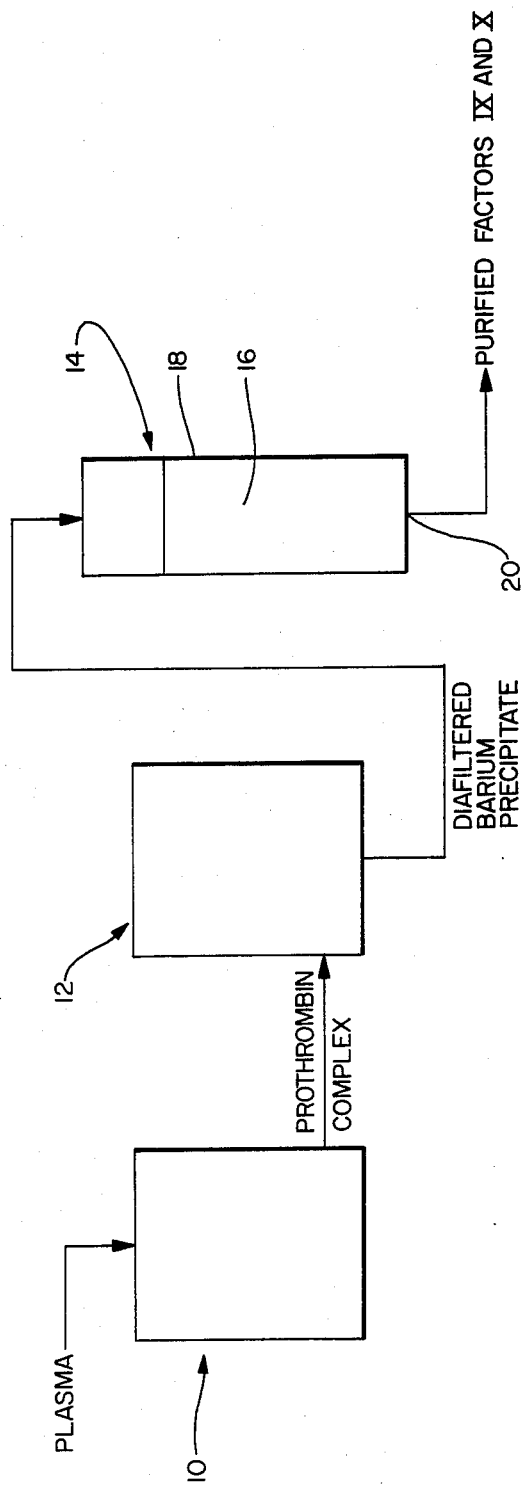

PLASMA FRACTION PURIFICATION USING SILICA RESIN BOUND TO A LIGAND

FIELD OF THE INVENTION

This invention relates to a method and apparatus useful for separation of Factor IX and/or Factor X from protein fractions such as those found in human plasma.

BACKGROUND OF THE INVENTION

Various biologic products are produced from biological materials, such as blood plasma, obtained from human and non-human sources. The various fractions of protein materials separated from human plasma that are useful as biologic products can include albumin, antithrombin III, Factor VIII (anti-hemophilic factor [AHF], and the prothrombin complex (PTC) which includes Factor IX, together with Factors II, VII and X.

Factor IX participates in the cascade of events that leads to blood coagulation. Factor IX is absent or deficient in patients who have a condition identified as "Hemophilia B". Thus, the blood of Hemophilia B patients does not clot properly. Factor IX is administered to Hemophilia B patients to provide sufficient Factor IX to return the clotting ability of their blood to as close to normal as possible.

The Factor IX concentrates that are presently available include other blood factors in addition to Factor IX. For example, the prothrombin complex mentioned above includes Factors II, VII and X in addition to Factor IX.

The occurence of thrombotic complications, such as deep vein thrombosis, disseminated intravascular coagulation (DIC) and pulmonary embolism has been reported in patients treated with prothrombin complex concentrates. These complications are frequently seen in premature infants, patients with poor liver function and surgery patients. They have also been observed in Hemophilia A patients receiving prothrombin complex concentrate as a Factor VIII inhibitor bypassing agent.

The thrombogenic component of prothrombin complex concentrates has most often been attributed to either activated Factors, coagulant active phospholipid or zymogen overload. Zymogen overload may be the basis of DIC in surgical situations where patients receive large and repetitive doses of prothrombin complex concentrates. In such cases, a buildup of zymogens in the circulation, particularly of prothrombin and Factor X, is likely to occur due to their relatively long half-life in relation to Factor IX.

Because of the thrombotic complications associated with the use of prothrombin complex, it is desirable to provide a Factor IX concentrate essentially free of other proteins for use in treating Hemophilia B patients.

In the human blood clotting cascade, Factor X in its active form (Factor Xa) cleaves prothrombin (Factor II) to form thrombin (Factor IIa). Thrombin then acts on fibrinogen to form fibrin which becomes the structural protein of the clot. Providing an external source of purified human Factor X or Xa may be desirable in the treatment of certain patients with bleeding disorders related to Factor X or other coagulation Factor deficiencies.

Various methods for enhancing the purity of Factor IX and/or Factor X concentrates have been reported. For example, processes for producing concentrates of Factor IX essentially free of prothrombin, Factor VII and Factor X by use of affinity chromatography on a sulfated dextran gel have been disclosed (D. Menache et al, "Coagulation Factor IX Concentrate: Method of Preparation and Assessment of Potential In Vivo Thrombogenicity in Animal Models", *Blood*, Vol. 64, No. 6, December, 1984, pp. 1220-1227). Factor IX has also been disclosed as having been purified by affinity chromatography on a heparin-Sepharose (agarose) gel (L-O. Andersson et al, "Purification and Characterization of Human Factor IX", *Thrombosis Research*, Vol. 7, 1975, pp. 451-459). Factor IX and Factor X have been separated by using a process which includes heparin-agarose chromatographic techniques (S. P. Bajaj et al, "A Simplified Procedure For Purification of Human Prothrombin Factor IX and Factor X", *Preparative Biochemistry*, 11(4), 1981, pp. 397-412). Procedures are also known in the art for separating Factor IX by affinity chromatography on a dextran sulfate-sepharose (agarose) gel.

While Factors IX and X can be separated on agarose gels in the laboratory, the use of agarose gels for large scale separations has been found to be unsatisfactory. When the agarose gels are put into commercial size columns, they compress to an undesirable extent and thereby inhibit flow of liquids through the column.

It is, therefore, desirable that a process for separation of Factor IX and/or Factor X from other proteins be provided that utilizes a chromatographic resin that has sufficient rigidity so that it can be used in large commercial size columns without causing a excessive pressure drop.

SUMMARY OF THE INVENTION

Practice of this invention provides a process for separation of Factor IX and/or Factor X from an impure protein fraction, for example, from a plasma fraction complex or from any recombinant derived materials containing Factor IX and/or Factor X and an apparatus for practicing the process. An aqueous solution of the impure protein fraction is provided. The impure protein fraction solution is applied to a chromatographic column containing a silica resin coupled with a ligand capable of binding Factor IX and/or Factor X. Factor IX and/or Factor X is bound to the ligand and the Factor IX and/or Factor X is then recovered from the column by elution.

BRIEF DESCRIPTION OF THE DRAWING

These and other features, aspects and advantages of the present invention will be more fully understood when considered with respect to the following detailed description, appended claims and accompanying drawing which is a block diagram showing a preferred embodiment of the process of the invention including a chromatographic column used in the final stage of the process.

DETAILED DESCRIPTION

The process provided in accordance with practice of principles of this invention relates to separation of Factors IX and/or X from an impure protein fraction. As used herein, an "impure protein fraction" means a protein fraction which includes one or more proteins in addition to Factor IX, when it is desired to separate Factor IX, and which includes one or more proteins in addition to Factor X when it is desired to separate Factor X. Referring to the drawing, a block diagram illustrating a preferred embodiment of the process of the invention including a chromatographic column used in the final stage of the process is shown. In a first stage 10 of the illustrated embodiment, human plasma is treated to separate and recover the prothrombin complex, which includes Factors II, VII, IX and X. In a second stage 12 of the illustrated embodiment, Factors IX and X are separated by barium citrate precipitation of the prothrombin complex recovered from the first stage. In a third and final stage, Factors IX and X in the barium precipitate are separated from Factors II and VII and from each other in a chromatographic column 14 containing a bed of silica resin coupled with a ligand capable of binding Factors IX and X. Preferably the ligand is dextran sulfate but other ligands such as dermatan sulfate, heparin, heparan sulfate or the like may also be used. If desired, the barium citrate precipitation stage can be eliminated and an aqueous solution of prothrombin complex from the first stage can be applied directly to the chromatographic column to separate the Factors IX and X from Factors II and VII and from each other.

Although the process of the invention is described below with reference to separation of Factors IX and X from prothrombin complex, the process is contemplated to be useful for separating Factors IX and X from other proteins as well.

SEPARATION OF PROTHROMBIN COMPLEX PROTEINS FROM HUMAN PLASMA

In the first stage 10 of the illustrated embodiment of the process of the invention, prothrombin complex proteins are separated from human plasma that has been collected and tested according to procedures approved by the U.S. Food and Drug Administration. The plasma is initially frozen at a temperature of about $-20°$ C. The plasma is then thawed at $0°$ C. to $+5°$ C. to allow cryoprecipitation to occur. The resulting plasma-cryoprecipitate mixture is pooled and centrifuged to remove the cryoprecipitate. The pooled AHF-poor plasma is then weighed, brought to $0°$ C. to $+5°$ C., and electrodialyzed to reduce the plasma sodium concentration from its original value to between 85 and 105 mM. The dialyzed AHF-poor plasma is then adjusted to about a neutral pH by the addition of acetic acid.

The prothrombin complex factors contained in the pH adjusted AHF-poor plasma are adsorbed by the addition of regenerated DEAE (diethyl aminoethyl) cellulose. The DEAE cellulose and the plasma are mixed approximately 30 minutes, and the DEAE cellulose is then collected by centrifugation. The DEAE cellulose-adsorbed prothrombin complex is washed with a buffer comprising about 0.03 M sodium phosphate and about 0.03 M sodium citrate at a pH of about 6.8. The wash is discarded.

The washed DEAE cellulose-adsorbed prothrombin complex is then removed from the centrifuge and suspended in a wash buffer. The resulting suspension is then poured into a column, and the eluate from the column is discarded. The column containing the DEAE cellulose is then washed with a wash buffer, and this wash is also discarded. The prothrombin complex factors are then eluted by washing the column with an eluting buffer comprising 0.03 M sodium phosphate, 0.03 M sodium citrate, and 0.2 M sodium chloride at a pH of about 6.8. The eluate is collected, and the prothrombin complex fractions are pooled and collected in a bulk solution. Appropriate tests of the collected prothrombin complex fractions are made and, after the pH of the bulk solution is adjusted to about neutral, the solution is filtered through a sterile bacteria-retentive cartridge or membrane to thereby form a bulk solution of filtered prothrombin complex. The bulk solution of filtered prothrombin complex is then lyophilized, and the lyophilized prothrombin complex powder is collected.

In one exemplary embodiment, the resulting dry prothrombin complex powder is dispersed in heptane. The volume of heptane used is at least twice the volume of the dry powder. The dispersion is then heated at a temperature of not less than $60°$ C. for a period of not less than 20 hours. The heat-treated powder is recovered from the heptane by filtration and is air dried to remove residual heptane. The dry, heat-treated prothrombin complex powder is placed in a container for further processing in accordance with the process of this invention. A dry heat treated prothrombin complex powder, identified by the trademark PROFILNINE ®, is produced, as described above, by Alpha Therapeutic Corporation of Los Angeles, Calif.

SEPARATION OF FACTORS IX AND X FROM PROTHROMBIN COMPLEX POWDER BY BARIUM CITRATE PRECIPITATION

In one exemplary embodiment of the second stage 12 of practice of this invention, dry, heat-treated prothrombin complex powder produced as described above, is dissolved in distilled water and is then diluted approximately 2-10 fold with a diluting buffer (sodium citrate, sodium chloride, pH $7.40 \pm 0.10$). If desired, prothrombin complex powder that has not been heat treated or which has been heat treated by methods other than the heptane method described above can be used. A volume of 0.5-2 M barium chloride solution sufficient to precipitate Factors IX and X is added to the dilute prothrombin complex solution. The precipitate is collected and dissolved in a solution of 0.2 to 0.6 M (Ethylenedinitrilo) tetra acetic acid (EDTA) and diafiltered against low sodium buffer (0-0.2 M NaCl in a solution buffered to between pH 6.0 and 9.0) to remove barium and EDTA and to obtain a desirably low sodium concentration for further processing.

It has been found that barium citrate precipitation of prothrombin complex yields an increase in the activity of Factor IX and X per unit weight of total protein in the resulting fraction of from about 1.2 to about 3.

In the third stage 14 of the process of the invention, the diafiltered barium precipitate is applied to a column containing a silica resin coupled with dextran sulfate. Factors IX and X are then recovered from the column by elution.

PREPARATION OF DEXTRAN SULFATE SILICA RESIN

In one exemplary embodiment of preparing a dextran sulfate silica resin useful in practice of principles of this invention, activated silica resin supplied by SERVA Fine Biochemicals Inc. of Westbury, N.Y., under the trademark CNBR SP500 was used. The resin is made up of spherical particles of from about 100 to 200 microns in size which contain channels with an average width from 40 to 80 nanometers (nm). The SP500 resin is supplied in its activated form having been activated by means of cyanogen bromide. While a resin having a particle size of from about 100 microns to about 200 microns is preferred, resins having a size of from about 1 micron to about 1000 microns can be used. If the resin has a particle size of less than about 1 micron, too high a pressure drop and undesirably low flow rates are encountered. If the resin size is larger than about 1000 microns the column has an undesirably low resolution resulting in less than desirable separation.

One kilogram (kg) of the CNBR activated silica resin was gently slurried with 2 kg of distilled water in a Buchner funnel and was then aspirated to dampness. The slurry/wash step was repeated twice more. A dextran sulfate solution was prepared by dissolving 10–200 grams of dextran sulfate in a buffered solution preferably 0.1 M $NaHCO_3$ (pH 8.3) and the washed silica resin and dextran sulfate solutions were combined and poured into baffled roller bottles or other mixing containers. The containers were then placed on a roller or other mixing apparatus and were tumbled from 1 to about 24 hours. This procedure resulted in the dextran sulfate ligand coupling with the activated silica resin. More than 1 kg of activated silica may be used as long as ratios of resin and dextran sulfate are as described above. The ligand-coupled resin was then washed with one or more volumes of distilled water in a Buchner funnel or other washing device and aspirated to dampness. The wash was repeated twice more. The ligand-coupled resin was then further washed with a solution containing 2.0–4.0 M NaCl at a pH of about 6–8. This wash was done in a Buchner funnel or other washing device and the resin was aspirated to dryness. This latter process was repeated several times and was followed by similiar washes and aspirations with one or more volumes of a buffered solution at pH 6–8 containing 0 to 0.2 M NaCl.

The washed ligand-coupled resin was then treated to thereby block any remaining active groups that had not combined with a ligand. During the blocking step, several resin volumes of a solution of normal serum albumin was combined with the washed ligand-coupled resin. Instead of using albumin, blocking of active groups can be accomplished by mixing the ligand-coupled resin with solutions containing glycine or other blocking agents known in the art. The suspension of albumin and ligand-coupled resin was placed into a mixing container and mixed from about 1 to 10 hours. The blocking solution was then washed off the blocked, ligand-coupled resin by washing the resin several times with distilled water in a Buchner funnel. The blocked ligand-coupled resin was then washed several times with one or more volumes of a solution containing 2.0–4.0 M NaCl at a pH of 6–8. A final wash with distilled water was provided and the resin was aspirated to dampness.

The final preparation step for the ligand-coupled resin included repeated washings with several resin volumes of "alcatone" (a solution of 50% by volume acetone 35% by volume ethanol and 15% by volume water). The slurry was stored at 2° C. to 8° C. prior to its use.

If desired, either non-activated silica or the non-activated polyol derivative of silica can be used as the starting material instead of activated silica, and the silica may be activated by cyanogen bromide activation using processes known in the art. Also, if desired, instead of dextran sulfate, the ligand coupled to the activated silica can be dermatan sulfate, heparin, heparan sulfate or an other ligand having a similiar organic structure. If another such ligand is used, the procedure to couple it to the activated silica is essentially the same as the procedure described above for coupling dextran sulfate to the silica.

PREPARATION OF THE CHROMATOGRAPHIC RESIN AND COLUMN

In one embodiment of practice of the process of the invention, a 2 liter MODULINE ® chromatographic column supplied by Amicon Corporation of Danvers, Mass., was used. The column included an elongated hollow container 18 having an outlet 20 at its bottom. The ligand-coupled resin prepared as described above was decanted from the alcatone solution in which it was stored and was washed with distilled water at a pH of approximately 6.8 in a Buchner funnel. The resin was then slurried with a volume of distilled water to provide that the resin slurry volume did not exceed the total column volume, and the slurry was not so thick as to retain air bubbles. The bottom of the column was filled with from 1 to 2 centimeters of distilled water at the temperature at which the column is to be run and the resin slurry was added to the column by pouring it down the side wall. The slurry was mixed thoroughly and the outlet 20 of the column was opened to drain it. The resin was then packed into the column by pumping distilled water through the column at a selected rate. The flow rate was adjusted 20 to 30% higher than the flow rate expected during operation, i.e., from about 0.15 to about 0.5 liters per minute, and the pumping was continued until the resin was completely packed in the column. Once the resin was completely packed, the distilled water pump was turned off and the components of the column were tightened into place.

To prepare the column for separation of Factors IX and X from a prothrombin complex solution comprising Factors IX and X, the column was washed with distilled water followed by a wash with a low sodium buffer, i.e., a buffer containing between 0 and 0.25 M sodium chloride at a pH of from 6 to about 9. Five to 10 column volumes of low sodium buffer were pumped from a flask through the column using a pump with a variable flow control.

SEPARATION OF FACTORS IX AND X FROM HEAT TREATED PROTHROMBIN COMPLEX POWDER

In an exemplary embodiment of the process of this invention, the amount of ligand-coupled resin in the chromatographic column is determined to be adequate to absorb all of the Factor IX in a diafiltered barium precipitate. Usually between 1 and 4 liters of dextran sulfate silica resin are required for every 0.10 kg of dry, heat-treated prothrombin complex powder being processed.

A solution containing the diafiltered barium precipitate is prepared as described above. The solution is then pumped through the dextran sulfate silica resin in the column so that the Factor IX and a portion of the Factor X contained in the solution is adsorbed into the resin. After the adsorption step is completed, the Factors IX and X adsorbed on the resin are washed with a volume of wash buffer approximately equal to three times the volume of resin in the column. Factors IX and X are then eluted from the resin by flowing a linear salt (sodium chloride) gradient through the column. The gradient is formed by gradually increasing the amount of sodium chloride which is present in the column wash buffer. When the salt (sodium chloride) concentration is less than about 0.2 M. Factor X is eluted from the column essentially in the absence of Factor IX. At a concentration of from about 0.25 M to about 0.4 M, both Factors IX and X are eluted. When the salt gradient reaches a concentration of about 0.4 M, the eluant contains essentially only Factor IX. At the completion of the salt gradient, the column is further eluted by washing with a wash buffer containing the maximum level of sodium chloride used in the gradient, e.g., 0.5 M. The Factor IX containing eluate and the Factor X containing eluate are separately pooled, and either immediately further processed or frozen and held for later processing. The Factor IX or Factor X eluates may be filtered prior to further processing or freezing.

The dextran sulfate silica resin can be reused repeatedly. The resin in the column is either reused immediately or is washed with a 2-4 M sodium chloride solution followed by water and alcatone. After washing, the resin can be stored at from 2° C. to 8° C. in alcatone for future use.

When the Factor IX pooled eluates from several runs have been accumulated, eluates are thawed (if frozen), combined, and the pH is adjusted to about neutral. This combined pool is then diafiltered to obtain the correct target parameters of Factor IX activity and sodium concentration. The pH is checked, and readjusted if necessary. If desired, the Factor IX or Factor X eluates may be reapplied to the column for further purification. The solution is filtered using previously sterilized bacteria retentive cartridge or membrane filters.

The Factor IX sterile bulk is sampled for sterility and Factor IX activity. Fill volume is calculated based upon Factor IX activity. The sterile bulk is filled into clean sterilized vials, frozen and dried under vacuum, stoppered and sealed. The freeze dried final container Factor IX is then tested by quality control. When test results are within all applicable specifications, quality control releases the lot.

The same procedure described above for Factor IX can also be used for Factor X, if desired.

EXAMPLE 1
SEPARATION OF FACTOR IX FROM HEAT TREATED PROTHROMBIN COMPLEX POWDER

In one example of practice of this invention for separation of Factor IX from heat-treated prothrombin complex powder, 85 grams of such prothrombin powder produced as described above was reconstituted with approximately 1.2 kg of cold water for irrigation (CWFI). The reconstituted prothrombin powder was diluted with 4.8 kg of 4° C. dilution buffer (0.02 M sodium citrate, 0.25 M sodium chloride, pH 7.4) and mixed for 20 minutes at 2° C.-4° C. About 960 milliliters (mL) of 1.0 M barium chloride solution (4° C.) was added over the course of 8 minutes and the mixture was then stirred for an additional 1 hour The mixture was kept at between 2° C. and 4° C. during the addition of barium chloride and during mixing. After mixing, the solution was centrifuged in a Sharples centrifuge keeping the flow rate through the centrifuge between 0.2 and 0.5 liters per minute and the temperature of the solution between 2° C. and 6° C. Approximately 0.347 kg of barium citrate precipitate was collected in this manner. About 1.2 kg of a 0.4 M (ethylenedinitrilo) tetra acetic acid (EDTA) solution at 20° C.-25° C. was added to dissolve the precipitate, and the precipitate was filtered through a Millipore CPX-10C filter to remove particulates. After filtration the solution was passed through a concentrator provided by Millipore Corporation of Bedford, Mass. identified as a Millipore Pellicon ® concentrator and was concentrated to between 1/5 and 1/10 of its original volume. The concentrated solution was then diluted to its original volume with a solution containing 0.02 M sodium citrate, at pH 6.8. The concentration and dilution steps were repeated six more times, at which point the conductivity of the solution was approximately equal to that of the 0.02 M sodium citrate solution. After the final dilution, the weight of the diafiltered material was 0.9 kg.

This material was applied at a flow rate of about 30 mL/min to a 9 cm×38 cm Moduline chromatographic column containing dextran sulfate silica resin, prepared as described above and which had previously been equilibrated with a solution containing 0.02 M sodium citrate at pH 6.8. After the material had entered the column, 12 kg of a 0.2 M sodium citrate solution, pH 6.8 was passed through the column. Two kilograms of this solution were applied at a flow rate of 30 mL/min, followed by 10 kg at about 100 mL/min. Immediately after washing the column as described above, a 12 liter linear salt gradient from 0.05 M NaCl to 0.5 M NaCl in a 0.02 M sodium citrate solution (pH 6.8) was applied to the column at a flow rate of 100 mL/min. Three-tenths liter aliquots of the column eluent were collected during the gradient and each fraction was assayed to determine its Factor IX and Factor X activity. After the gradient, an additional 1 liter of the solution containing 0.02 M sodium citrate and 0.5 M sodium chloride was applied to the column, and 0.5 liter aliquots of the eluent were collected and assayed for Factor IX and X activity. Those aliquots containing relatively high Factor IX activity and relatively low Factor X activity were pooled to form a Factor IX eluate pool. The Factor IX eluate pool was concentrated by diafiltration using the Millipore Pellicon concentrator and the sodium concentration was adjusted to approximately 150 milliequivalents per liter by addition of a 0.02 M sodium citrate solution, pH 6.8.

After concentration and sodium adjustment, the Factor IX eluate was filtered through a (sterile) 0.2 micron filter and dispensed into 20 mL glass vials (approximately 8 mL per vial). The contents of the vials were then frozen and lyophilized. This material was used for in vivo thrombogenicity studies.

Material from each stage of the purification process was assayed for Factor IX activity and protein content. The results of these assays are shown in Table I. The lyophilized Factor IX eluate was assayed to determine the relative amounts of Factors II, VII, IX and X. It was found that for every 100 units of Factor IX present, there were 0 units Factor II, 11 units of Factor VII and 10 units of Factor X.

TABLE I

|  | Total Units | Yield | Factor IX specific activity (Units/mg) |
|---|---|---|---|
| Prothrombin Complex Concentrate | 69,460 (81,380) | 100% (100%) | 5 assay 1 (assay 2) |
| Barium Precipitate | 89,800 (55,600) | 100% (70%) | 8 assay 1 (assay 2) |
| Factor IX eluate pool-preconcentrate | 37,670 | 54% |  |
| Factor IX eluate pool-concentrated | 31,880 | 46% | 180 |
| Factor IX eluate | 17,840 | 26% | — |

TABLE I-continued

|  | Total Units | Yield | Factor IX specific activity (Units/mg) |
|---|---|---|---|
| Lyophilized |  |  |  |

EXAMPLE 2

SEPARATION OF FACTOR X FROM HEAT TREATED PROTHROMBIN COMPLEX

The procedure of this example is the same as the procedure of Example 1 except that Factor X was separated instead of Factor IX. Aliquots containing relatively high Factor X activity and relatively low Factor IX and Factor II activity were pooled to form a Factor X aliquot pool. Material from the starting prothrombin complex concentrate, the barium citrate precipitate and a concentrated Factor X aliquot pool where assayed for Factor X activity and protein content. The results of these assays are shown in Table II. The purity of Factor X was increased 1.5 fold by barium precipitation and an additional 5.1 fold by chromatography on the dextran sulfate silica column.

TABLE II

|  | Total Units | Yield | Factor X specific activity (Units/mL) |
|---|---|---|---|
| Prothrombin Complex Concentrate | 47,208 | 100% | 2.5 |
| Barium Precipitate | 31,410 | 67% | 3.8 |
| Factor X eluate pool, concentrated | 3,900 | 8% | 19.4 |

EXAMPLE 3

THROMBOGENICITY OF PREPARATIONS OF PTC AND PURIFIED FACTOR IX

Male New Zealand rabbits weighing about 2 kg were used in this experiment. The rabbits were anesthetized with 6.2% sodium pentobarbital injected into the right marginal ear vein at a dose of about 0.5 mL per kg of weight. Lyophilized prothrombin complex PROFIL-NINE ® (Lot No. B90620B) or Factor IX concentrates prepared in accordance with practice of this invention, and as set forth in Example 1, were dissolved with sterile water for injection to a concentration of 100 units per mL of Factor IX.

This material was then administered as a rapid bolus through the left ear vein and blood stasis was produced by ligation of the right jugular vein either 30 seconds later (for prothrombin complex concentrate assays) or 1 minute later (for Factor IX concentrate assays). Fifteen minutes after stasis induction, the venous segment was opened in situ, examined and a thrombosis reported as being either present or absent. The dose of prothrombin complex was administered on a dose per kg of body weight basis.

Referring to Table III, results of the testing are shown. When prothrombin complex concentrate was tested in this system, none of the rabbits in the test showed evidence of a thrombus at a dose of 30 units/kg. However, thrombus formation was observed in animals receiving doses of prothrombin complex concentrate between 40 and 50 units/kg. When three lots of purified Factor IX concentrate prepared in accordance with practice of this invention were tested in the rabbit stasis system, none were found to be thrombogenic even at doses up to 500 units/kg.

TABLE III

|  |  | Dose (units/kg) | | | | | | |
|---|---|---|---|---|---|---|---|---|
|  |  | 30 | 50 | 100 | 200 | 300 | 400 | 500 |
| Prothrombin Complex Concentrate |  | 0/7 | 3/4 | 4/4 |  |  |  |  |
| Purified Factor IX | Lot 1 |  |  |  |  |  | 0/2 |  |
|  | Lot 2* |  |  |  |  | 0/4 |  |  |
|  | Lot 3 |  |  |  |  |  |  | 0/2 |

(Thrombogenicity is reported as: animals with thrombus/animals tested)
*Lot 2 Factor IX concentrate was the material prepared in Example 1.

In addition to elution of Factor IX and/or Factor X from the column by a linear salt gradient, elution may be accomplished by washing, through the column, buffered solutions containing increasing amounts of NaCl in a step-wise manner. Also, if desired, binding of Factor IX and/or Factor X to the silica resin and elution from the resin by washing the resin with buffers containing increasing amounts of NaCl can be performed outside of the column. In this case, suitable means for separating the protein solution and washing solutions from the resins, such as decanting or centrifugation, is required.

The above description of preferred embodiments of processes for separating Factor IX and/or Factor X from impure protein fractions containing Factor IX and/or Factor X, and an apparatus useful for practicing the separation processes, is for illustrative purposes. Because of variations which will be apparent to those skilled in the art, the present invention is not intended to be limited to the particular embodiments described above. The scope of the invention is defined in the following claims.

What is claimed:

1. A process for separating Factor IX from an impure protein fraction containing Factor IX, the process including the steps of:
   providing an aqueous solution of the impure protein fraction;
   applying the impure protein fraction solution to a chromatographic column containing a silica resin coupled with a ligand capable of binding Factor IX;
   binding Factor IX to the ligand; and
   recovering Factor IX from the column.

2. The process according to claim 1 wherein the ligand is dextran sulfate.

3. The process according to claim 1 wherein the ligand is heparin.

4. The process according to claim 1 wherein the ligand is dermatan sulfate.

5. The process according to claim 1 wherein the ligand is heparan sulfate.

6. The process according to claim 1 wherein the impure protein fraction is prothrombin comprising Factor II, Factor VII, Factor IX and Factor X.

7. The process according to claim 1 wherein the silica resin has a particle size of from about 1 micron to about 1000 microns.

8. The process according to claim 1 wherein the silica resin has a particle size of from about 100 microns to about 200 microns.

9. A process for separating of Factor X from an impure protein faction containing Factor X, the process including the steps of:

providing an aqueous solution of the impure protein fraction;

applying the impure protein fraction solution to a chromatographic column containing a silica resin coupled with a ligand capable of binding Factor X;

binding Factor X to the ligand; and recovering Factor X from the column.

10. The process according to claim 9 wherein the ligand is dextran sulfate.

11. The process according to claim 9 wherein the ligand is heparin.

12. The process according to claim 9 wherein the ligand is dermatin sulfate.

13. The process according to claim 9 wherein the ligand is heparan sulfate.

14. The process according to claim 9 wherein the impure protein fraction is prothrombin comprising Factor II, Factor VII, Factor IX and Factor X.

15. The process according to claim 9 wherein the silica resin has a particle size of from about 1 micron to about 1000 microns.

16. The process according to claim 9 wherein the silica resin has a particle size of from about 100 microns to about 200 microns.

17. A process for separating Factor IX from an impure protein fraction containing Factor IX, the process including the steps of:

preparing an aqueous solution of the impure protein fraction;

preparing a silica resin coupled with a ligand capable of binding Factor IX;

applying the impure protein fraction solution to the ligand-coupled silica resin;

binding Factor IX to the ligand; and recovering Factor IX from the resin.

18. the process according to claim 17 wherein the ligand is dextran sulfate.

19. The process according to claim 17 wherein the ligand is heparin.

20. The process according to claim 17 wherein the ligand is dermatan sulfate.

21. The process according to claim 17 wherein the ligand is heparan sulfate.

22. The process according to claim 17 wherein the impure protein fraction is prothrombin comprising Factor II, Factor VII, Factor IX and Factor X.

23. A process for separating of Factor X from an impure protein faction containing Factor X, the process including the steps of:

preparing an aqueous solution of the impure protein fraction;

preparing a silica resin coupled with a ligand capable of binding Factor X;

applying the impure protein fraction solution to the ligand coupled silica resin;

binding Factor X to the ligand; and recovering Factor X from the resin.

24. The process according to claim 23 wherein the ligand is dextran sulfate.

25. The process according to claim 23 wherein the ligand is heparin.

26. The process according to claim 23 wherein the ligand is dermatan sulfate.

27. The process according to claim 23 wherein the ligand is heparan sulfate.

28. The process according to claim 23 wherein the impure protein fraction is prothrombin comprising Factor II, Factor VII, Factor IX and Factor X.

* * * * *